United States Patent
Radley et al.

(10) Patent No.: US 8,699,662 B2
(45) Date of Patent: *Apr. 15, 2014

(54) DETERMINATION OF COMPOSITION OF LIQUIDS

(75) Inventors: Ian Radley, Bishop Auckland Durham (GB); Max Robinson, Shincliffe Durham (GB); Gary Gibson, Esh Winning Durham (GB)

(73) Assignee: Kromek Limited, Sedgefield (GB)

( * ) Notice: Subject to any disclaimer, the term of this patent is extended or adjusted under 35 U.S.C. 154(b) by 628 days.

This patent is subject to a terminal disclaimer.

(21) Appl. No.: 12/988,978

(22) PCT Filed: Mar. 24, 2009

(86) PCT No.: PCT/GB2009/050271
§ 371 (c)(1),
(2), (4) Date: Jan. 24, 2011

(87) PCT Pub. No.: WO2009/130492
PCT Pub. Date: Oct. 29, 2009

(65) Prior Publication Data
US 2011/0110493 A1 May 12, 2011

(30) Foreign Application Priority Data
Apr. 24, 2008 (GB) .................................. 0807474.2

(51) Int. Cl.
*G01N 23/083* (2006.01)
*H05G 1/64* (2006.01)

(52) U.S. Cl.
USPC .............................. 378/53; 378/57; 378/98.9

(58) Field of Classification Search
USPC .......... 378/51, 53, 57, 91, 92, 98, 98.8, 98.9, 378/204, 210; 250/306–308, 370.01, 250/370.06, 370.11, 370.13, 393–395, 428, 250/432 R, 433, 440.11, 491.1, 493.1, 250/494.1, 526
See application file for complete search history.

(56) References Cited

U.S. PATENT DOCUMENTS

| | | | | |
|---|---|---|---|---|
| 3,818,232 A | * | 6/1974 | Kirkpatrick | 378/52 |
| 3,845,963 A | * | 11/1974 | Price | 279/89 |
| 5,493,596 A | | 2/1996 | Annis | |
| 6,246,747 B1 | * | 6/2001 | Wear et al. | 378/98.9 |

(Continued)

FOREIGN PATENT DOCUMENTS

| | | |
|---|---|---|
| DE | 102005049586 | 4/2007 |
| JP | 60-113135 | 6/1985 |

(Continued)

OTHER PUBLICATIONS

International Search Report and Written Opinion, dated Aug. 3, 2009, 13 pages.
JP Office Action, 2011-505595, Jun. 25, 2013, 9 pages (including translation and identifying the pertinence of each reference).

*Primary Examiner* — Anastasia Midkiff
(74) *Attorney, Agent, or Firm* — Drinker Biddle & Reath LLP (57) ABSTRACT

A method of and apparatus for obtaining radiation transmission data from a liquid in such manner that allows some data about relative proportions of constituent ingredients to be derived is described. A radiation source and a radiation detector system able to resolve transmitted intensity across a plurality of frequencies within the spectrum of the source are used to produce transmitted intensity data for each such frequency. Measured data is compared numerically to a mass attenuation data library storing mass attenuation data, individually or collectively, for a small number of expected constituent ingredients of the liquid to fit each intensity data item to the relationship given by the exponential attenuation law: $I/I_O = \exp[-(\mu/\rho)\rho t]$ in respect of the constituent ingredients and derive therefrom an indication of relative proportions of each constituent ingredient.

17 Claims, 2 Drawing Sheets

(56) References Cited

U.S. PATENT DOCUMENTS

| | | |
|---|---|---|
| 2006/0203956 A1 | 9/2006 | Raupach |
| 2007/0092056 A1 | 4/2007 | Flohr et al. |
| 2007/0144268 A1* | 6/2007 | Atkinson .................. 73/861.63 |
| 2007/0147584 A1 | 6/2007 | Hofman |

FOREIGN PATENT DOCUMENTS

| | | |
|---|---|---|
| JP | 61-128145 | 6/1986 |
| JP | 06-121791 | 5/1994 |
| JP | 2007-127611 | 5/2007 |
| WO | WO 2008/007976 | 1/2008 |

* cited by examiner

DETERMINATION OF COMPOSITION OF LIQUIDS

FIELD OF THE INVENTION

The invention relates to an apparatus and method for the determination of the composition of liquids. The invention in particular relates to an apparatus and method making use of high energy radiation such as x-rays or gamma-rays to scan contained liquids or liquid samples where it is desirable to gain information about the composition of a liquid sample.

The invention is especially suited to the determination of the composition of a liquid where its general identity and likely component ingredients are generally known, but where the precise proportions of those likely component ingredients represent an unknown in a given sample.

BACKGROUND

Many techniques and technologies have been proposed for creating machines that can automatically determine liquid composition, such as x-ray diffraction, x-ray scattering, Mossbauer spectroscopy and NQR. Often, these have been proposed for or led by security applications, for example to detect explosive or contraband liquids, but similar considerations also arise in other circumstances where it might be desirable to gain information about the internal composition of a contained liquid or liquid sample, for example for identification purposes, for stock control or quality control purposes, to monitor changes and especially degradation over time, and other applications. In particular, x-ray systems have been used to produce images of and give limited information about contraband and other liquids.

X-Ray absorption has been used for some time as the basis for screening objects to create some form of representational image of the contents or components thereof relative to each other in three-dimensional space. The thicker or more dense an object is then the more it will attenuate an x-ray beam. By use of suitable detectors and a suitable source, radiographs of an item under screening in the form of images based on the absorption of an object or set of objects can be generated. In airline security applications, the principle is encountered in particular in relation to hand baggage scanners.

X-Ray absorption has been used to a limited extent for materials identification. It is known that the x-ray absorption properties of any material can vary spectroscopically, and that this effect depends in particular on atomic number. This has led to development of dual-band or dual-energy detectors which are capable of separately identifying low- and high-energy bands from the full spectrum of x-ray emissions.

A dual energy system confers only limited information about composition. Recent development of detectors that can resolve spectroscopic information about the transmitted x-rays more effectively has led to the development of apparatus that discriminate across a larger range of bands and generate a larger plurality of images across these bands to generate multispectral images. However, it remains a problem to distinguish multiple materials in a transmission path.

SUMMARY OF THE INVENTION

It is an object of the present invention to mitigate some or all of the above disadvantages of prior art scanning systems and methods.

Therefore, according to one aspect of the invention there is provided an apparatus for determination of information regarding the composition of a liquid sample comprising:

a radiation source and a radiation detector system spaced therefrom to define a scanning zone therebetween and to collect in use a dataset of information about radiation incident at the detector and hence transmissivity of an object in the scanning zone;

a data processing apparatus to process and resolve such dataset spectroscopically across a plurality of frequencies/frequency bands within the spectrum of the source to produce an intensity data item for each frequency or band;

a mass attenuation data library storing mass attenuation data for a plurality of expected constituent ingredients of the liquid;

a comparator, for example including calculation means to perform successive calculations, to fit each intensity data item to the relationship given by the exponential attenuation law:

$$I/I_0 = \exp[-(\mu/\rho)\rho t]$$

in respect of the constituent ingredients and derive therefrom an indication of relative proportions of the constituent ingredients in a transmission path producing the said intensity data items.

Preferably, the comparator comprises a calculation means adapted to derive and fit to the data in the data library an overall mass attenuation coefficient for each intensity data item, for example in that it is adapted to: derive an intensity data item at its respective frequency; read an ingredient mass attenuation coefficient for each such ingredient at the said frequency; repeat at sufficient frequencies that a single unique solution can be derived to fit the relative proportions of each constituent ingredient to the said intensity data items.

However, other alternative means of storing and processing mass attenuation data, individually or collectively, for a plurality of expected constituent ingredients of the liquid will readily suggest themselves. For example a database may contain information on the overall mass attenuation coefficients of a range of samples consisting of different ratios of the individual constituent components. It would then be possible to look for the best match between the sample under test and the database. Moreover, if a standard test container was provided, as discussed in further detail below, it would be possible simply to track the intensity change against frequency/energy to find the best fit.

By analogy, in accordance with a second aspect of the invention there is provided a method of obtaining radiation transmission data and determining therefrom information about the composition of a liquid sample comprising the steps of:

providing a radiation source and a radiation detector system spaced therefrom to define a scanning zone therebetween and to collect in use a dataset of information about radiation incident at the detector and hence transmissivity of an object in the scanning zone;

positioning a liquid sample in the scanning zone, operating the source, and collecting one or more datasets of intensity information about radiation incident at the detector system and hence transmissivity of the sample in the scanning zone from radiation transmitted through the sample and received at the detector system;

resolving such intensity dataset across a plurality of frequencies/frequency bands within the spectrum of the source to produce intensity data item for each frequency or band;

comparing the intensity data items to a mass attenuation data library storing mass attenuation data for a plurality of expected constituent ingredients of the liquid to fit each intensity data item to the relationship given by the exponential attenuation law:

$$I/I_0 = \exp[-(\mu/\rho)\rho t]$$

in respect of the constituent ingredients and derive therefrom an indication of relative proportions of the constituent ingredients in a transmission path producing the said intensity data items.

Preferably the step of comparing the intensity data items comprises deriving an overall mass attenuation coefficient for each intensity data item at its particular frequency and fitting the dataset of such calculated mass attenuation coefficients to data from the library and for example carrying out the steps of:

deriving an overall mass attenuation coefficient for an intensity data item at its particular frequency;

reading an ingredient mass attenuation coefficient for each such ingredient at the said frequency;

repeating for a plurality of data items at a sufficient number of frequencies that a single unique solution can be derived for the relative proportions of each constituent ingredient necessary to produce the said intensity data items.

However, the method will by analogy with the above encompass alternative means of storing and processing mass attenuation data, individually or collectively, for the plurality of expected constituent ingredients, for example in that the database may contain information on the overall mass attenuation coefficients of a range of samples consisting of different ratios of the individual constituent components with the comparison step then comprising fitting to the best match between the sample under test and the database. The measured data is thus fitted numerically and for example iteratively to the stored library data until and over sufficient different frequencies that a relative proportion solution is derived.

The radiation source of the example comprises a source to deliver high-energy radiation such as ionizing radiation, for example high energy electromagnetic radiation such as x-rays and/or gamma rays, or subatomic particle radiation, and the detection system is adapted correspondingly to detect radiation in this spectrum.

In accordance with the invention, intensity data from transmitted x-rays, gamma rays or the like is thus collected in a generally conventional manner. For each "scanning event" (that is, for a measurement of transmitted intensity via a given transmission path through a given liquid sample in a given position) an "intensity dataset" is collected representing the transmitted intensity across at least part of a source energy spectrum. However, the key to the invention is that a detection system is used which is capable of detecting intensity data for a given "scanning event" into a plurality, and for example at least three, separate frequencies (whether as discrete single frequencies or frequency bands) across the spectrum of the source. An intensity dataset thus constitutes a dataset of intensity information related to frequency/energy which is resolvable into such bands to produce a plurality of intensity data measurements or data items relating to a given scanning event and hence a given transmission path through the liquid sample.

The transmission of radiation through a material can be given by the exponential attenuation law, as follows:

$$I/I_0 = \exp[-(\mu/\rho)\rho t]$$

$\mu/\rho$ = Mass attenuation coefficient.

A material constant which is characteristic of the weighted elemental composition of a material or component ingredient I = Final intensity
$I_0$ = Initial intensity
$\rho$ = density of the material
t = thickness of the material For each scanning event, a plurality of resolved intensity data item measurements are obtained numerically to provide representative information which can be correlated to the mass attenuation coefficient necessary to produce such an intensity pattern. As is described in greater detail below, most of the variables associated with a given scanning event are constant with respect to the frequency/energy of the incident radiation from the source. However, the mass attenuation coefficient varies with energy in characteristic way. Thus, inferences relating to the specific mass attenuation coefficient applicable to the transmission path through material under test for a given scanning event can be drawn for each intensity data item (i.e. at each frequency band).

A comparison is then made to a suitable database library of data representative of the mass attenuation coefficient for different ingredients to give a more representative indication of what is being scanned.

The key to methodology of the invention lies in the realisation that in many instances the general identity of a liquid under test, and its general composition in the sense of its major likely constituent ingredients, are both known. What is not known is the precise proportion of those major ingredients.

In accordance with the invention, for a given target type of liquid under test, a relatively small number of major ingredients are identified, at least in general terms, which together can be expected to constitute essentially the whole liquid in practice, save for minor trace constituents, and thus can be expected collectively to contribute essentially to the entire transmission response of the liquid during transmission testing. A mass attenuation coefficient data library stores mass attenuation coefficients representative of each of these ingredients.

It should be understood that where used herein the term "ingredient" may refer to a single identifiable chemical species, or to a constituent made up of a number of individual chemical species of the same general class or which are otherwise to be collectively identified, provided that such a compound constituent can be separately identified by development of general characteristic mass attenuation coefficient data for storage in the data library, in the manner of the invention. For example, in the case of organic liquids it might be desirable to determine for a liquid, such as milk, data for overall fat content, overall protein content, overall sugar content or the like, using stored library data for the generalised mass attenuation behaviour of milk fats, milk proteins, milk sugar, or milk solids in the generality.

The key to the invention is that the majority of the parameters in the equation set out above are known, either to the extent that is necessary for the materials to be distinguished from the data library of mass attenuation coefficients, or from measurement, or are constant for the source and are therefore constant as between each intensity data item at a different frequency for a given scanning event. In particular, a scanning experiment is arranged such that the "thickness" of the liquid overall (that is, the distance of the ray path through the sample) is known, either by measurement at the outset or by using a standard specimen container into which a liquid is decanted to test.

Thus, in the given relationship, an overall and spectrally resolved $I_0$ is known for the source, an overall sample thickness t is known, a value of $\mu/\rho$ is stored for each likely ingredient, and a spectrally resolved overall I is derived at a plurality of frequencies or frequency bands.

In this way, a scan can be performed where the only underlying variable is the overall mass attenuation coefficient. This can be determined from I and $I_0$. At a single frequency, all that can be determined is this overall mass attenuation coefficient for the sample. However, the invention is applicable top situations where the presence only of a small number of identified likely ingredients can be presumed, each exhibiting its own characteristic functional variation of mass attenuation coefficient with radiation frequency. The contribution of each ingredient can be given by its effective contribution to the value of t, which can be seen, if the liquid sample is fully mixed and any constituent evenly distributed, to relate directly to its proportion by volume in the overall composition. The unknown can be rendered as the relative proportion of each contribution, and hence the relative proportion of each ingredient. By taking measurements at sufficient different frequency bands and performing a suitable iterative comparative process in the calculation means, this unknown can be eliminated and the plurality of intensity data items can be fitted to the single ingredient ratio capable of producing the observed relationship.

Data is resolved spectroscopically over a sufficient plurality of frequencies or frequency bands to derive such a unique ingredient ratio. Where only two potential ingredients are present, spectral resolution into two bands only may be sufficient in theory, although more complete spectral resolution is always likely to be preferred. Where there are more ingredients it will be necessary to resolve the spectrum more completely before a unique ratio can be correlated to the plurality of data items. Nevertheless, in accordance with the invention, provided a relatively small number of likely ingredients can be identified for the target sample under test, a correspondingly relatively small number of intensity data items can be used to derive useful information about the ratio between those ingredients.

The apparatus of the invention has a comparator that effects a comparison between the stored data in the data library and the derived data from the scan, and in particular includes calculation means at least to calculate a mass attenuation coefficient for each intensity data item and compare and fit the same to the library data. Any suitable form of comparator combining suitable hardware and software, and for example a suitably programmed data processing apparatus such as a suitably programmed general purpose or special purpose computer, can be envisaged.

It will be understood generally that each numerical step in the method of the invention can be implemented by a suitable set of machine readable instructions or code. These machine readable instructions may be loaded onto a general purpose computer, special purpose computer, or other programmable data processing apparatus to produce a means for implementing the functions specified, and in particular to produce a comparator or calculation means as herein described.

These machine readable instructions may also be stored in a computer readable medium that can direct a computer or other programmable data processing apparatus to function in a particular manner, such that the instructions stored in a computer readable medium produce an article of manufacture including instruction means to implement some or all of the steps in the method of the invention. Computer program instructions may also be loaded onto a computer or other programmable apparatus to produce a machine capable of implementing a computer executed process such that the instructions are executed on the computer or other programmable apparatus providing steps for implementing some or all of the steps in the method of the invention. It will be understood that a step can be implemented by, and a means of the apparatus for performing such a step composed in, any suitable combinations of special purpose hardware and/or computer instructions.

The precise scanning geometry of the apparatus in the invention is not pertinent to its operation in accordance with the invention. For example, scanning systems are known which involve both a static relationship between test object and source/detector and relative movement between test object and source/detector, in the latter case either by having a movable scanner arrangement or by having a movable object. Scanning systems are known which scan an object in a plurality of different positions, in particular for example to generate an image. The principles of the invention are applicable to all such apparatus, but the invention requires merely a single source, a single ray path, and a dimensionless detector, to generate the necessary information. For simplicity therefore a static system is likely to be preferred.

Preferably, the apparatus is adapted to collect in use transmission intensity data with a liquid sample or object that may contain a liquid sample in a single scanning position and for example includes a means to retain a liquid sample or object in a scanning position such as a receptacle into which a liquid sample or object, and for example a liquid container, can be placed. Additionally or alternatively it may include a conveyor to convey a liquid sample or object into and out of such scanning position.

In particular, the apparatus is adapted to receive a sample under test comprising a liquid in a container of other material, such as a bottle, flask, carton or the like, and comprises a container receiving means adapted to receivingly support a container within the scanning zone. The container receiving means may include holding means to hold the container static in situ. These may adjust to hold containers of different sizes. Adjustable and for example spring loaded formations may be provided to effect this.

Similarly, the method of the invention preferably comprises placing a sample under test in the scanning zone and supporting it in the scanning zone on sample retention means. In particular, the method is applicable to a sample under test comprising a liquid in a container of other material, such as a bottle, flask, carton or the like, and the method comprises placing a container under test in the scanning zone and supporting it in the scanning zone on sample retention means comprising container holding means.

The above analysis is based on a presumption that the thickness term "t" in the above equation is not an unknown. Accordingly, in one possible embodiment, the container is a standard test container of known material, and of known internal dimensions, and is adapted to seat in a fixed position relative to a scanner and detector in order to present a defined ray path lane through a liquid contained therein in use during a test. Additionally or alternatively, the method may comprise, in a step to be performed prior to scanning the liquid, a step of determination of the properties of an empty container, and in particular the measurement of the transmission characteristics of the empty container and/or a step of measurement of the ray path distance defined by the internal volume of the empty container in position for use.

For example, a blank test may be performed on an empty container prior to a full test on a container with liquid content. Additionally or alternatively, the apparatus may be provided with distance measurement means, for example in the form of a laser range finder.

In this way, prior to performance of the test, knowledge is obtained both of the likely contribution to the transmitted dataset of the absorptivity of any container and the variable "t" in the above equation.

Conveniently, a standard container provided in accordance with an apparatus of the invention is fabricated of material which is relatively transmissive across the spectrum of the source. A plurality of containers, to accommodate a plurality of different sample sizes, may be provided.

Conveniently, the apparatus of the invention is adapted to receive a sample under test, and preferably to hold it in a static position in the scanning zone, in that it comprises a container receiving means adapted to receivingly support a container within the scanning zone. Preferably, the container receiving means includes holding means to hold the container static in situ. Preferably the holding means are adjustable to hold containers of different sizes.

The detector system is adapted to generate spectroscopic information about the transmitted radiation at least to the extent of resolving a plurality of and preferably at least five discrete energies or energy bands. Preferably, the detector exhibits a spectroscopically variable response across at least a substantial part of the spectrum of the radiation source allowing detailed spectroscopic information to be retrieved.

The detector system is capable of being used to detect and derive an intensity data item from a plurality of resolved frequencies/bands. So long as they are resolved, the bandwidth is not directly pertinent to the invention and useful results can be obtained by any suitable approach to dividing the spectrum, either in whole or in part, into separate bands. For example, the entire spectrum or a substantial part thereof may simply be divided between such a plurality of bandwidths, and each data item be considered as a measure representative of intensity across the entire band, and for example an average intensity. Alternatively, a plurality of relatively wide bands, but with discrete gaps therebetween, may be envisaged and analysed on the same basis. Alternatively, "bands" may be narrow even to the point where they essentially approximate to an evaluation of intensity at a single energy. As used herein the concept of intensity at an energy or frequency "band" includes evaluation of intensity at such a discrete single energy as well as evaluation of intensity at an energy across a narrow or broad bandwidth.

The radiation source must produce a distribution of energies across a suitable spectral range for characteristic scattering, and is typically an x-ray source. Tungsten is the most appropriate target, but others could be used.

The source may be a single broad spectrum source across which a plurality of bandwidths or single energies may be identified. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source comprises an x-ray source having a relatively lower energy spectrum, for example operating below 60 keV and for example at 10 to 50 keV and one or more radioisotope sources generating radiation at higher energies, for example above 100 keV.

If we consider the exponential attenuation equation, it can be seen that the mass attenuation coefficient is one of the terms listed. The mass attenuation coefficient itself is however dependent on the energy of the detected x-rays. The other terms in the equation have no dependence on the x-ray energy. Thus if one measures transmission at multiple energies it is possible to relate the variation in transmission functionally to the mass attenuation coefficient.

As this term is characteristic of each material present it is therefore possible in principle given sufficient data items to derive the relative contributions of each ingredient in a particular target liquid by fitting each variation to the dataset of total transmitted intensities (and to a dataset of total calculated mass attenuation coefficients at each energy, ie for each intensity data item) to derive a ratio of ingredients uniquely that fits the measured transmitted intensity dataset and the dataset of total calculated mass attenuation coefficients.

Information regarding total transmitted intensity, and thus pertinent to the mass attenuation coefficient inherent in the dataset for a given scanning event, and hence the composition of liquid in a transmission path, can be obtained by a single scanning event, for example of a stationary sample being scanned by a single beam of appropriate geometry, for example a pencil beam or conical beam. In such circumstance the method merely includes placing the sample in a scanning zone to obtain such a single scan.

Although mobile scanners and scanners with an imaging functionality are not precluded by our outside the scope of the invention they are not a necessary requirement for operation of the method.

At its most basic, the invention allows compositional analysis of liquids from collected transmission data based on a numerical analysis, with reference to a suitable data library of equivalent or otherwise comparable data for a known and limited range of ingredients likely to be encountered in a given target. The data library may comprise information in any suitable form which can be related in a numerically analytical manner to data collected across the resolved energy bands in accordance with the invention. The data library may include standard preset reference materials and/or user input reference materials and/or reference data may be generated from known materials in accordance with the foregoing method. That is, a library of data may be built up by the system, which can in effect "learn" material characteristics, over time. The data library may comprise electronically stored data and/or data stored on a hard medium, such as a printed resource, and may be held and accessed locally and/or remotely, manually and/or automatically, none of which is directly pertinent to the operation of the method of the invention.

Although reference has been made hereinabove to a liquid sample, it will be appreciated that in most practical situations the liquid will be within a container, which may be a standard container with known properties or not. For example, a single liquid sample may be tested, by being placed in a test container of known composition. In an alternative situation, contained liquid samples, in bottles, jars, cartons or the like, may be presented for screening.

Providing the container material contribution is known in advance or can be identified, either analytically by data processing in the above manner, or by becoming otherwise known, and for example then input into the system, the contribution of the container to the result produced by the foregoing ratio analysis can be identified and subtracted from the result, so that the result more accurately reflects the material properties of the liquid alone. The ray path ("t" in the above equation) can also be eliminated as a variable. Thus, in an embodiment of the method particularly applicable to a liquid sample within a non-standard container, the method involves in an additional step seeking to identify the material composition of the container, whether by analysis of transmitted intensity or otherwise, and modifying the analytical result on the basis of such identification so that it represents more closely the sole contribution of the liquid within the container prior to making a final comparison step with the database.

An essential requirement for implementation of the invention is that the detector system can generate spectroscopic information about the transmitted radiation. That is, the detector exhibits a spectroscopically variable response across at least a substantial part of the breadth of the radiation spectrum of the source allowing spectroscopic information to be retrieved. This is resolved across at least three energy bands and a numerical analysis above described is performed to obtain information representative of the material content in a transmission path. Thus, in accordance with the invention a genuine and much more specific identification of a target material or narrow class of materials is possible.

A detector system in accordance with the invention may comprise a single detector or a plurality of discrete detector elements making up a multi-element system. In contrast with imaging systems, the present invention does not require spatial resolution, but in practice operates a zero-dimensional intensity only analysis. For simplicity, a single detector may therefore be preferred.

Preferably, a detector system, or some or all discrete detector elements making up a multi-element system, may be adapted to produce spectroscopic resolution in that it exhibits a direct spectroscopic response. In particular a system or element is fabricated from a material selected to exhibit inherently as a direct material property a direct variable electrical and for example photoelectric response to different parts of the x-ray spectrum. For example, the detector system or element comprises a semiconductor material or materials preferably formed as a bulk crystal, and for example as a bulk single crystal (where bulk crystal in this context indicates a thickness of at least 500 μm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_b Te$ where a and/or b may be zero.

Combinations of these and any other such materials may be considered which give spectroscopic resolution of transmitted radiation.

A collimator is preferably provided to produce an emitted beam of suitable geometry from the x-ray source. At its simplest, particularly if the apparatus is being used purely to collect spectrally resolved transmission data for the purposes of deriving numerically an indication of mass attenuation coefficient, a simple, effectively one dimensional beam may be provided in conjunction with a simple single transmission detector.

BRIEF DESCIPTION OF THE DRAWINGS

The invention will now be described by way of example only with reference to the accompanying drawings in which.

DESCRIPTION OF THE PREFERRED EMBODIMENTS

Figure 1:
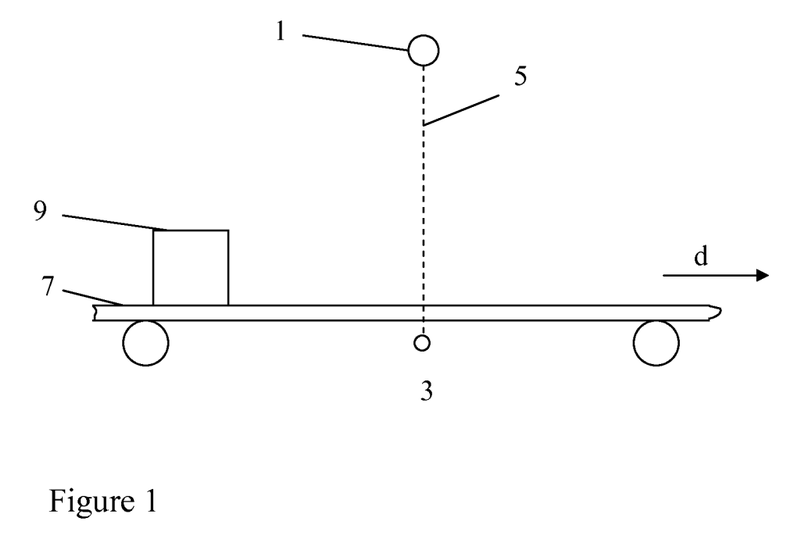
FIG. 1 is a side view of a representation of a scanning apparatus suitable for use in an embodiment of the invention.

Referring to FIG. 1, a suitable x-ray source 1 is used to direct x-rays via a scanning zone in the direction of a detector 3.

In the illustrated embodiment in figure one, the scanner is a mobile scanner (that is, it is adapted to create relative movement between the scanning system and an object under test). Such relative movement is entirely immaterial to the performance of the present invention, but may be useful for example if a secondary, imaging function to produce a transmission radiograph is required.

With this dual application in mind the illustrated embodiment uses a single an x-ray source collimated to produce a curtain beam incident upon a linear detector (which in the embodiment each comprises a linear array of detector elements) which can be used to develop a radiograph.

In the embodiment, detector 3 comprises material capable of spectroscopic resolution of incident x-rays, and in the specific example comprises cadmium telluride although the skilled person will appreciate that other material selections may be appropriate. To exploit this spectral resolution, the x-ray source emits x-ray across a broad energy spectrum. In the example a tungsten source is used, although the skilled person would appreciate that other materials might be appropriate.

An endless belt conveyor 7 causes an object to be scanned 9 to move in a direction d so as to intercept the ray path in the scanning zone.

Datasets of transmitted intensity information are generated by building up transmitted information from the detector. The dataset of information may be processed by resolving, at least to some extent, a relationship between incident energy/wavelength and transmitted intensity for both numerical analysis in accordance with the principles of the invention and spectroscopically resolved imaging purposes.

Thus, the principles of the invention are applicable to existing scanning systems which also have an imaging function, provided detectors are used which can spectroscopically resolve the transmitted radiation for the numerical analysis of the invention. However, for most practical purposes, a simple static detector is likely to be preferred, particularly since it is likely to allow greater control over the operational parameters of the scanning process. Such an apparatus is illustrated schematically in FIG. 2.

Figure 2:
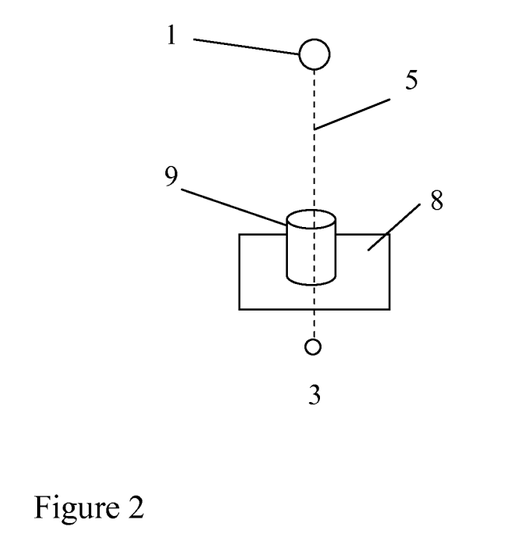
FIG. 2 is a side view of a representation of an alternative scanning apparatus suitable for use in an embodiment of the invention.

Referring to FIG. 2, a suitable x-ray source 1 is used to direct x-rays via a scanning zone in the direction of a detector 3.

The detector again comprises material capable of spectroscopic resolution of incident x-rays, and in the specific example comprise cadmium telluride although the skilled person will appreciate that other material selections may be appropriate. To exploit this spectral resolution, the x-ray source emits x-ray across a broad energy spectrum.

The system shall comprise an x-ray generator and set off detector arrays. When the container is placed in the system and the door closed the operator shall initiate the x-ray scan by means of a single push button.

The illustrated embodiment additionally uses a plural source comprising an x-ray source collimated to produce a pencil beam with a designed spectrum of operation of around 10 to 50 keV and at least one higher energy radioisotope source, for example at above 100 keV. In the example a 122 keV cobalt-57 source is provided. These are illustrated as a co-located single source 1 in the figure. Discrete multiple sources 1 and detectors 3 may be provided.

A container of liquid 9 is retained under test in sample holder 7, such that a ray path 5 is incident upon it. The attenuation of the beam shall be measured by the detector set and a material analysis shall take place which indicates the status of the liquid in the container. In the preferred embodiment, the container is of known dimensions, and of a known material which does not absorb x-rays too strongly to interfere with the transmitted signal from the liquid. The sample holder 7 retains the container 9 in a fixed and defined position within it. It follows that the container 9 is held in a fixed and known relationship with the source and detector, and thus a fixed and consistent ray path is defined through a liquid contained within it. It also follows that the effective "thickness" of the sample in a ray path direction, the term "t" in the attenuation equation set out hereinabove, is a known quantity.

Because the apparatus is design only to produce a single spectroscopically resolved data set, and does not require multiple ray paths, relative movement between object and scanning system, or other such complexity as might be required for generation of a radiograph, the apparatus can be kept simple, and is for example compact and portable, with a single discreet source and a single discreet, effectively dimensionless single pixel, detector.

Figure 3:
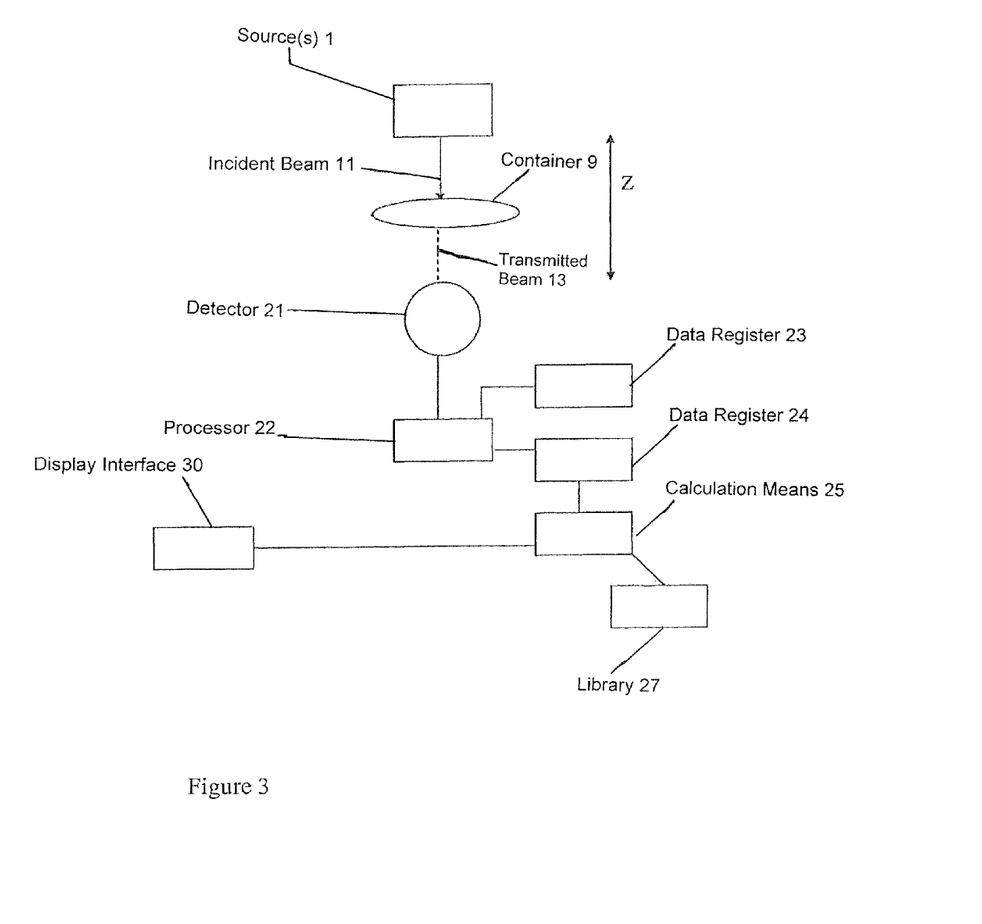
FIG. 3 is general schematic of a possible apparatus to implement the invention including a scanner of FIG. 1 or 2.

A dataset of transmitted intensity information is generated by resolving, at least to some extent, a relationship between incident energy/wavelength and transmitted intensity for numerical analysis in accordance with the principles of the invention as is illustrated in FIG. 3.

In the general schematic representation on FIG. 3 a source 1 and laterally spaced detector apparatus assembly 21 together define a scanning zone Z between them. In use, a liquid sample to be scanned is held in the scanning zone as above.

An incident beam 11 from the source is illustrated. In this simple schematic, the incident beam is represented by the line 11. The transmitted beam 13 is incident upon a detector 21.

The detector 21 is in data communication with a processor 22. The inherent spectral resolution of the material allows the processor 22 to resolve this image differentially across a plurality of pre-set frequency/energy bands in accordance with the principles of the invention by reference to energy band boundaries stored in the data register 23.

In the example embodiment a plural x-ray and radioisotope source is used. The x-ray spectrum may be resolved across several frequency bands and information supplemented by information at each radioisotope source energy. For illustration in the example, intensity information at five energies/bands is thus resolved. In practice, the number of different energies/energy bands as the case may be into which the spectrum needs to be resolved, and the number of different intensity data items at different energies which need to be thus derived, will depend on the number of variables in the equation to which the data needs to be fitted, and consequently upon the number of ingredients whose presence needs to be identified or discounted, and whose proportion needs to be derived.

The processor 22 acts in relation to each of the series of identified x-ray energy bands/discrete radioisotope energies and uses the data to generate a representative quantification of, and for example in the case of a band an average of, transmitted intensity, which is then passed to the intensity data item register 24 for storage.

A calculation means 25 compares the data thereby produced with a library of data 27. The library of data includes pre-stored data of similar or at least numerically comparable nature which is related to or depends upon the mass attenuation coefficient for a small number of specified target ingredients for a given liquid under test.

Any of the data processing or storage elements of the apparatus, for example including one or more of the processor 22, data register 24, calculation means 25 and library 27 may be provided by a suitably programmed data processor means such as a special purpose or general purpose computer.

The library may also include data on commonplace liquid container materials and structures. This may be a manually or automatically addressed library. Data may be preloaded or referenced, or may be generated or added to over time by operation of the apparatus with known materials.

By virtue of this comparison, inferences may be drawn about the likely liquid content in the transmission path and in particular about the likely proportion of ingredients. This may be displayed on the operator display interface 30.

This is effected in that the calculation means 25 is adapted to perform an iterative calculation to fit the measured data to the library by deriving a weighting for the relative contribution of each ingredient, and hence a measure of the proportional content. The mass attenuation equation which is applied is set out hereinabove. If the apparatus is used in accordance with the principles of the invention, it can be seen that all of the variables therein are known either from the container (which defines "thickness" of the sample) or from the source (which is of a fixed initial intensity and known spectrum). The mass attenuation coefficients of each ingredient likely to make any substantive contribution to the overall transmission intensity are also known. The overall mass attenuation coefficient at a given frequency can be readily determined numerically by the calculation means 25 from the intensity data set. What is not known, at any single given frequency, is the contribution of each individual ingredient to that overall attenuation. However, the mass attenuation coefficient of each ingredient varies characteristically and differently with energy. Accordingly, it is at least possible in principle, by fitting the data for all the known mass attenuation coefficients for all the ingredients to the calculated value at each energy, to derive a unique solution for the relative proportions of each ingredient. This unique solution can be delivered to the output means 30.

In this way, in accordance with the invention, provided general knowledge of the likely constituents of a liquid under test is available, and data concerning these likely constituents can be stored, relative compositional information can be obtained.

In one particular envisaged application, the apparatus is envisaged as being used to test organic liquids to obtain information their general constituent components. For example, it might be desirable to determine the fat, or sugar, or protein content of milk. In such an example the liquid being presented for test is generally known. It is milk. The component ingredients whose relative proportions are to be determined are known. They are its aqueous base, emulsified fats, protein solids etc. Generally representative mass attenuation data for each such constituent can be stored, and thus relative levels measured according to the above numerical principles. For example, the invention can be used to measure fat content.

As the illustrated example shows, the particular strength of the invention lies in its ability to derive general indications about ingredient content to a sufficient degree of accuracy for practical purposes, in a simple and effective manner, without necessarily requiring full chemical compositional analysis. Provided the library of mass attenuation data can store a reasonably representative indication of the functional variation of mass attenuation with incident radiation energy for each component of a liquid system to be separately identified, it is not relevant to the invention whether such a component is a single chemical species, or a class of related or unrelated chemical species. Proportions may still be distinguished. For example, in the given example in relation to milk, if it was desirable merely to measure fat content, then provision in the data library of mass attenuation data representing as a first ingredient "milk fat" and as a second ingredient "the rest of milk" is likely to be sufficient to allow the relative proportions of such ingredients to be determined in accordance with the principles of the invention.

The invention claimed is:

1. An apparatus for determination of information regarding the composition of a liquid sample comprising:
   a radiation source and a radiation detector system spaced therefrom to define a scanning zone therebetween and to collect in use a dataset of information about radiation incident at the detector and hence transmissivity of an object in the scanning zone from radiation transmitted through the sample and received at the detector system;
   the radiation detector system being capable of generating spectroscopic information about the transmitted radiation in that the detector exhibits a spectroscopically variable response allowing spectroscopic information to be retrieved;
   sample retention means adapted to hold a liquid sample in a static position in the scanning zone comprising at least one standard container of known radiation transmission properties and size in which a liquid sample under test may be contained in use and a container receiving means adapted to receivingly support the standard container in a static position within the scanning zone;
   a data processing apparatus to process and resolve such dataset spectroscopically across at least three frequencies within the spectrum of the source to produce an intensity data item for each frequency;
   a mass attenuation data library storing mass attenuation data for a plurality of expected constituent ingredients of the liquid;
   a comparator to fit each intensity data item to the relationship given by the exponential attenuation law:

$$I/I_o = \exp[-(\mu/\rho)\rho t]$$

in respect of the constituent ingredients and derive therefrom an indication of relative proportions of the constituent ingredients in a transmission path producing the said intensity data items.

2. An apparatus in accordance with claim 1 wherein the comparator comprises a calculation means adapted to:
   derive an overall mass attenuation coefficient for an intensity data item at its frequency;
   read an ingredient mass attenuation coefficient for each such ingredient at the said frequency;
   repeat at sufficient frequencies that a single unique solution can be derived to fit the relative proportions of each constituent ingredient to the said intensity data items.

3. An apparatus in accordance with claim 1 wherein the container receiving means includes holding means to hold the container static in situ.

4. An apparatus in accordance with claim 3 wherein the holding means are adjustable to hold containers of different sizes.

5. An apparatus in accordance with claim 1 wherein the radiation source is a source of x-rays and/or gamma rays.

6. An apparatus in accordance with claim 1 wherein the radiation source is a plural source comprising a combination of sources at different energies to provide the necessary total spectrum spread to allow resolution by the detector across a plurality of energy bands.

7. An apparatus in accordance with claim 6 wherein the plural source comprises an x-ray source having a relatively lower energy spectrum, and one or more radioisotope sources generating radiation at relatively higher energies above 100 keV.

8. An apparatus in accordance with claim 1 wherein the detector system comprises a single detector and the beam from the source is collimated to produce a single essentially one dimensional beam.

9. An apparatus in accordance with claim 1 wherein a detector is adapted to produce spectroscopic resolution in that it is fabricated from a material selected to exhibit inherently as a direct material property a direct variable electrical response to different parts of the x-ray spectrum.

10. An apparatus in accordance with claim 9 wherein the detector comprises a semiconductor material selected from cadmium telluride, cadmium zinc telluride (CZT), cadmium manganese telluride (CMT), germanium, lanthanum bromide, or thorium bromide.

11. An apparatus in accordance with claim 9 wherein the detector comprises a semiconductor material or materials formed as bulk crystal including a Group II-VI semiconductor material.

12. An apparatus in accordance with claim 11 wherein the detector comprises a semiconductor material selected from cadmium telluride, cadmium zinc telluride (CZT), or cadmium manganese telluride (CMT).

13. A method of obtaining radiation transmission data useful for the identification and detection of composition of a liquid comprising the steps of:
   providing a radiation source and a radiation detector system spaced therefrom to define a scanning zone therebetween and to collect in use a dataset of information about radiation incident at the detector and hence transmissivity of an object in the scanning zone from radiation transmitted through the sample and received at the detector system, the radiation detector system being capable of generating spectroscopic information about the transmitted radiation in that the detector exhibits a spectroscopically variable response allowing spectroscopic information to be retrieved;
   providing sample retention means adapted to hold a liquid sample in a static position in the scanning zone comprising at least one standard container of known radiation transmission properties and size in which a liquid sample under test may be contained in use and a container receiving means adapted to receivingly support the standard container in a static position within the scanning zone;
   positioning a liquid sample in the sample retention means in the scanning zone, operating the source, and collecting one or more datasets of intensity information about radiation incident at the detector system and hence transmissivity of the sample in the scanning zone from radiation transmitted through the object and received at the detector system;
   resolving such intensity dataset across of at least three frequencies within the spectrum of the source to produce an intensity data item for each frequency;
   comparing the intensity data items numerically to a mass attenuation data library storing mass attenuation data for a plurality of expected constituent ingredients of the liquid to fit each intensity data item to the relationship given by the exponential attenuation law:

$$I/I_o = \exp[-(\mu/\rho)\rho t]$$

in respect of the constituent ingredients and derive therefrom an indication of relative proportions of the constituent ingredients in a transmission path producing the said intensity data items.

14. A method in accordance with claim 13 wherein the step of comparing the intensity data items comprises:
- deriving an overall mass attenuation coefficient for an intensity data item at its frequency;
- reading an ingredient mass attenuation coefficient for each such ingredient at the said frequency;
- repeating at sufficient frequencies that a single unique solution can be derived for the relative proportions of each constituent ingredient necessary to produce the said intensity data items.

15. A method in accordance with claim 13 comprising placing a sample under test in the scanning zone and supporting it in the scanning zone on the sample retention means.

16. A method in accordance with claim 13 comprising providing a plural radiation source comprising a combination of sources at different energies to provide the necessary total spectrum spread to allow resolution by the detector across a plurality of energy bands.

17. A method in accordance with claim 16 wherein the plural source comprises an x-ray source having a relatively lower energy spectrum and one or more radioisotope sources generating radiation at relatively higher energies.

\* \* \* \* \*

UNITED STATES PATENT AND TRADEMARK OFFICE
CERTIFICATE OF CORRECTION

PATENT NO.        : 8,699,662 B2                                                                                   Page 1 of 1
APPLICATION NO.   : 12/988978
DATED             : April 15, 2014
INVENTOR(S)       : Radley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 718 days.

Signed and Sealed this
Twenty-ninth Day of September, 2015

Michelle K. Lee
*Director of the United States Patent and Trademark Office*